(12) United States Patent
Comely et al.

(10) Patent No.: US 7,645,910 B2
(45) Date of Patent: Jan. 12, 2010

(54) PROCESS FOR THE PREPARATION OF AROMATIC DERIVATIVES OF 1-ADAMANTANE

(75) Inventors: Alexander Christian Comely, Barcelona (ES); Marta Marfil Sánchez, Barcelona (ES); Llorenç Rafecas Jané, Barcelona (ES); Xavier Verdaguer Espaulella, Barcelona (ES)

(73) Assignee: Finorga SAS, Chasse Sur Rhone (FR)

( * ) Notice: Subject to any disclaimer, the term of this patent is extended or adjusted under 35 U.S.C. 154(b) by 0 days.

(21) Appl. No.: 12/095,376

(22) PCT Filed: Dec. 1, 2006

(86) PCT No.: PCT/IB2006/054547

§ 371 (c)(1),
(2), (4) Date: Oct. 17, 2008

(87) PCT Pub. No.: WO2007/063522

PCT Pub. Date: Jun. 7, 2007

(65) Prior Publication Data

US 2009/0137841 A1    May 28, 2009

(30) Foreign Application Priority Data

Dec. 2, 2005    (ES) .............................. 200503050

(51) Int. Cl.
C07C 41/00    (2006.01)
C07C 25/00    (2006.01)

(52) U.S. Cl. .................. 568/632; 570/183; 570/184
(58) Field of Classification Search .................. None
See application file for complete search history.

(56) References Cited

U.S. PATENT DOCUMENTS 4,717,720 A * 1/1988 Shroot et al. .................. 514/63

FOREIGN PATENT DOCUMENTS

| EP | 0199636 A1 | 10/1986 |
| WO | 2006108717 | * 10/2006 |
| WO | WO 2006/108717 A | 10/2006 |

* cited by examiner

Primary Examiner—Karl J Puttlitz
(74) Attorney, Agent, or Firm—Millen, White, Zelano & Branigan, P.C.

(57) ABSTRACT

Process for the obtaining of 1-adamantane (tricycle[3.3.1.1 (3,7)]decane) derivatives, or of a pharmaceutically acceptable salt thereof, based on a carboxylation reaction, via metallation, of a precursor compound with an adequate leaving group. It also comprises the preparation of the precursor compound by means of a selective coupling of the corresponding boron, magnesium or zinc derivative with the corresponding disubstitute aromatic derivative. It is especially useful for the obtaining of Adapalene at industrial scale with good yield and high purity.

2 Claims, No Drawings

PROCESS FOR THE PREPARATION OF AROMATIC DERIVATIVES OF 1-ADAMANTANE

The present invention is related to a process for obtaining aromatic derivatives of 1-adamantane, in particular of Adapalene, from intermediate halogenated aromatic compounds. It is also related to a process for the preparation of said intermediates.

BACKGROUND ART

Adapalene is the International Nonproprietary name (INN) of an pharmaceutical ingredient, the chemical name of which is 6-[3-(1-adamantyl)-4-methoxyphenyl]-2-naphtoic acid, and which has the formula (Ia):

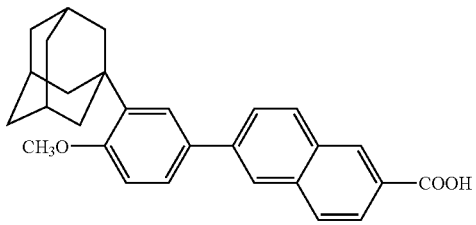

(Ia)

Adapalene is an antiacne agent, derived from naphthoic acid, with antiinflammatory and keratolityc properties.

Patent application EP 199.636-A1 describes benzonaphthalenic derivatives and their therapeutic and cosmetic utility. It is also describes a process for their preparation. Among the compounds described are several 1-adamantane derivatives, such as Adapalene, which is obtained by transforming the 2-(adamantyl)-4-halogen anisol into its magnesium, lithium or zinc derivative, followed by coupling with methyl 6-bromo-2-naphthoate and subsequent hydrolysis of the obtained ester in basic conditions. This process presents the drawback that the halogenated derivatives of the methyl naphthoate are difficult to prepare and are obtained with low yields.

On the other hand, patent application WO 01/56563-A1 describes several aromatic derivatives of 1-adamantane, including Adapalene and its use for the treatment and/or prevention of cancer.

Therefore, from what is known in the state of the art, it is derived that the provision of an alternative process for the preparation of aromatic derivatives of 1-adamantane which is efficient and of easy industrialization, would be of great interest for the industrial preparation of these compounds.

SUMMARY OF THE INVENTION

Inventors have found a new easy and simple process to prepare 1-adamantane derivatives, based on the incorporation at the end of the synthesis a carboxylic group into 1-adamantane derivatives of the halogenated aromatic kind. In particular, the process is especially advantageous for the preparation of Adapalene, from new 1-adamantyl benzonaphthalenic derivatives, obtained from commercial and common halogenated naphthalenes, since it is avoided to have to prepare naphthalenecarboxylic derivatives which are expensive and difficult to prepare derivatives.

Therefore, according to an aspect of the present invention, it is provided a process for preparing a compound of formula (I) or a pharmaceutically acceptable salt thereof,

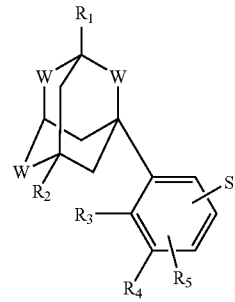

(I)

wherein W is a biradical selected from the group consisting of: —$CH_2$—, —O—, and —$SO_2$—; $R_1$ and $R_2$ are radicals, the same or different, independently selected from the group consisting of H, halogen, and ($C_1$-$C_6$)-alkyl; $R_3$ is a radical selected from the group consisting of hydroxyl, acyl, amide, halogen; ($C_1$-$C_6$) alkyl optionally substituted by one or more hydroxyl or acyl groups, and ($C_1$-$C_4$)-alkoxyl optionally substituted with one or more hydroxyl, ($C_1$-$C_4$)-alkoxyl groups or amide, and/or optionally interrupted by one or more oxygen atoms; $R_4$ is a radical selected from the group formed by H, hydroxyl, ($C_1$-$C_6$)-alkyl, and ($C_1$-$C_4$)-alkoxyl, or $R_3$ and $R_4$ form together a biradical —$OCH_2O$—; $R_5$ is a radical selected from the group consisting of H, ($C_1$-$C_6$)-alkyl, ($C_1$-$C_4$)-alkoxyl, and an halogen; S is a radical selected from (S)-1 and (S)-2,

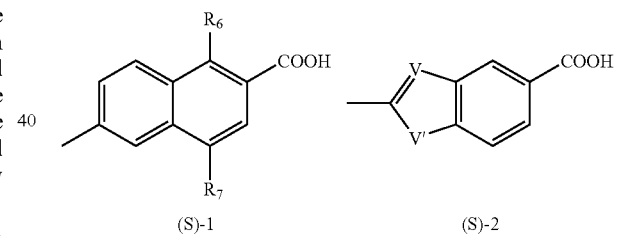

(S)-1  (S)-2 wherein $R_6$ is a radical selected from H, ($C_1$-$C_6$)-alkyl, and halogen; $R_7$ is a radical selected from H, hydroxyl, and halogen; V is a biradical —CH— and V' is an O atom; or V is a N atom and V' is a biradical —NH—; said process comprises to submit a compound of formula (II),

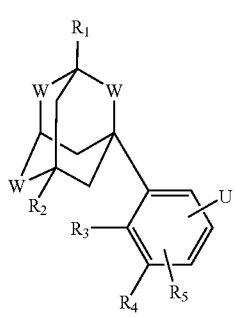

(II)

wherein U is a radical selected from (U)-1 and (U)-2:

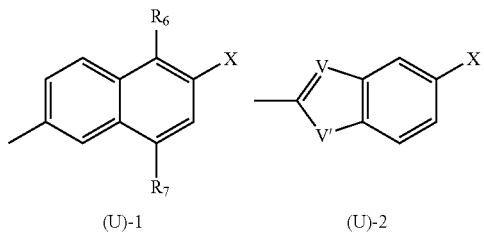

(U)-1  (U)-2 wherein: X is a leaving group adequate to carry out a metallation/carboxylation; and W, V, V', $R_1$, $R_2$; $R_3$, $R_4$, $R_5$, $R_6$, and $R_7$ have the same meaning as defined before; to a reaction of carboxylation which comprises the metallation of said compound of formula (II) using a metallation agent, followed by treatment with carbon dioxide, optionally carrying out a treatment with an acid, and optionally, converting the compound obtained after the acid treatment into a pharmaceutically acceptable salt thereof.

In a preferred embodiment, the compound of formula (I) is Adapalene (Ia) and the compound of formula (II) is the compound of formula (IIa) wherein X is a leaving group adequate to carry out a metallation/carboxylation.

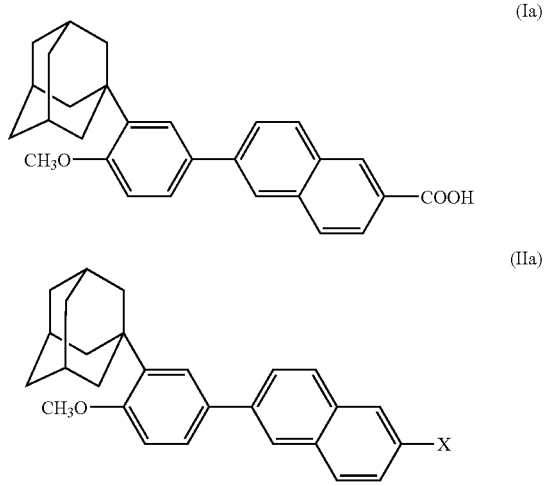

(Ia)

(IIa)

In a more preferred embodiment, X is selected from Cl, Br and I, and more preferably X is Br.

As an example, Scheme (1) summarizes the preparation of Adapalene (Ia) from the compound of formula (IIa) with X=Br. Optionally, sodium hydride can be added to the reaction medium. Adapalene can be obtained by means of an acid treatment of the carboxylated product.

Scheme 1:

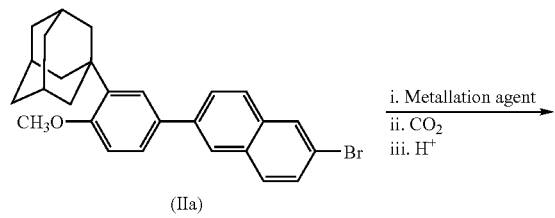

(IIa)

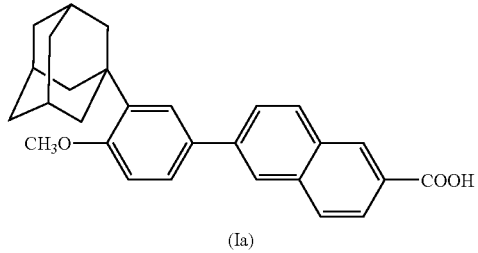

(Ia)

In another preferred embodiment, the metallation agent is a ($C_1$-$C_4$)-alkyl-lithium or magnesium. More preferably, is a ($C_1$-$C_4$)-alkyl-lithium, preferably selected from n-butyl lithium (n-BuLi) and terc-butyl lithium (t-BuLi).

Preferably, the metallation and the following treatment with $CO_2$ (gas or solid) is carried out at a temperature comprised between $-40°$ C. and $-78°$ C. More preferably, said process is carried out at a temperature comprised between $-40°$ C. and $-60°$ C. Also preferably the carboxylation is carried out in presence of an adequate solvent such as an ether, a ($C_6$-$C_8$) hydrocarbon or a mixture of the same. More preferably the solvent is tetrahydrofurane.

The conditions more adequate to carry out the reaction vary according to the parameters considered by the person skilled in the art, such as, for example, the solvent used, the metallation agent, temperature, time of metallation and the like. These conditions can be easily determined by said expert in the art by means of routine tests, and with the help of the instructions from the examples present in this document.

Finally, the compound of formula (I) obtained by means of the process of the present invention can be converted into pharmaceutically acceptable salts thereof, and the pharmaceutically acceptable salts can be converted into the free compound or into other pharmaceutically acceptable salts by means of conventional means described in the art.

According to another aspect of the present invention, it is provided a process for the preparation of the intermediate compound of formula (II) which comprises a coupling reaction between a compound of formula (III) and, either, the 2,4,6-tris[3-(1-adamantyl)-4-methoxyphenyl]-1,3,5,2,4,6-trioxatriborinane, or a compound of formula (IV)

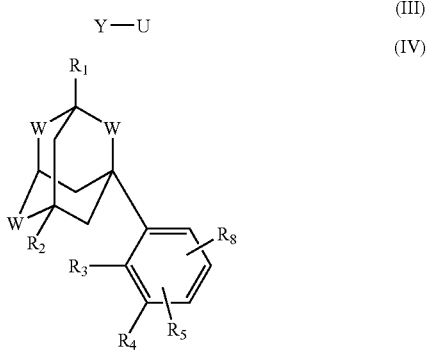

(III)

(IV)

where $R_8$ is a radical selected from MgZ, ZnZ and a radical of formula

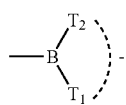

wherein Z is an halogen, preferably Cl and Br, and $T_1$ and $T_2$ are each independently selected from the group consisting of hydroxyl, $(C_1-C_4)$-alkoxyl and phenoxyl, this last optionally substituted by a $(C_1-C_4)$-alkoxyl group, $(C_1-C_4)$-alkyl group or an halogen; or alternatively $T_1$ and $T_2$ are taken together with the boron atom to form a cyclic structure selected from the following,

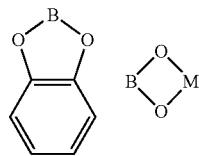

where M is selected from the group consisting of $(CH_2)_n$, $(CH_2)_rCR_uR_v(CH_2)_s$ and $CR_uR_v(CH_2)_tCR_uR_v$; n is an integral from 2 to 4; r and s are integers from 0 to 4 with the condition that r and s are not both 0; t is an integer from 0 to 1, and $R_u$ and $R_v$ are each independently selected from the group consisting of H, $(C_1-C_4)$-alkyl, phenyl, and mono- or di-substituted phenyl, being the substituents halogen, $(C_1-C_4)$-alkyl and $(C_1-C_4)$-alkoxyl.

In the formulas (III) and (IV) U, W, $R_1$, $R_2$, $R_3$, $R_4$, $R_5$, have the same meaning as defined before; Y is a leaving group adequate to carry out the coupling.

In the case of the boron derivatives, this reaction is known as the Suzuki coupling. Generally, it is carried out in presence of an adequate solvent and, preferably, in presence of a transition metal compound and a base. In the case of Zn derivatives, the reaction is known as the Negishi coupling.

In a preferred embodiment, the compound of formula (II) is the compound (IIa), and the coupling reaction is carried out between a compound of formula (IIIa) and, either, the 2,4,6-tris[3-(1-adamantyl)-4-methoxyphenyl]-1,3,5,2,4,6-trioxatriborinane or a compound of formula (IVa) wherein $R_8$ has the meaning described before;

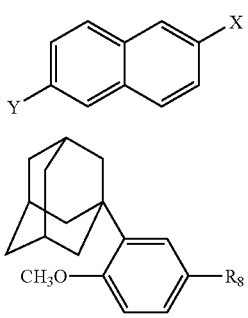

In the formula (IIIa), X represents a leaving group adequate to carry out a metallation/carboxylation, and Y is a leaving group adequate to carry out a coupling such as for example Cl, Br and I, or a sulphonate of formula $—OSO_2R_9$, wherein $R_9$ is a radical selected from $CF_3$, $(C_1-C_4)$-alkyl, phenyl and phenyl mono- or di-substituted by a radical selected from $(C_1-C_4)$-alkyl, halogen and nitro. Preferably the sulphonate is selected from mesylate ($R_9$=$CH_3$), tosylate ($R_9$=$C_6H_4CH_3$), besylate ($R_9$=$C_6H_5$) and triflate ($R_9$=$CF_3$), being the last the most preferred.

In a more preferred embodiment the starting compound of formula (IIIa) is that one in which Y is Br. In another preferred embodiment the starting compound of formula (IIIa) is that one in which Y is trifluoromethanesulphonate. In another preferred embodiment the starting compound of formula (III) is that one in which X is Br. Preferably, for the preparation of Adapalene the 2,6-dibromonaphthalene is used, which is a commercial product, or the 6-bromo-2-naphthalenyl trifluoromethanesulphonate. The last is easily prepared from the 6-bromo-2-naphthol by reaction with triflic anhydride, generally in the presence of a tertiary amine, such as triethylamine.

Preferably the compound of formula (IIIa) with Y=Br or trifluoromethanesulphonate and X=Br, is coupled with the 2,4,6-tris[3-(1-adamantyl)-4-methoxyphenyl]-1,3,5,2,4,6-trioxatriborinane or with a compound of formula (IVa) selected from 3-(1-adamantyl)-4-methoxyphenylboronic acid, [3-(1-adamantyl)-4-methoxyphenyl]-5,5-dimethyl-1,3,2-dioxaborinane and 3-(1-adamantyl)-4-methoxybenzene zinc chloride.

As an example, the lithiation of the commercial product 3-(1-adamantyl)-1-bromo-4-methoxybenzene, followed by treatment with triisopropyl borate $(B(O-i-Pr)_3)$ and acid hydrolysis, yields the 3-(1-adamantyl)-4-methoxyphenylboronic acid. This product can be converted into the cycled product 2,4,6-tris[3-(1-adamantyl)-4-methoxyphenyl]-1,3,5,2,4,6-trioxatriborinane by heating at about 60° C. or by means of a treatment with an aliphatic hydrocarbon $(C_6-C_8)$ such as for example hexane which can be carried out even at low temperature (0-5° C.).

The preparation of other boron derivatives of formula (IVa) such as the [3-(1-adamantyl)-4-methoxyphenyl]-5,5-dimethyl-1,3,2-dioxaborinane, can be carried out, for example, by the reaction of the product 2,4,6-tris[3-(1-adamantyl)-4-methoxyphenyl]-1,3,5,2,4,6-trioxatriborinane with the 2,2-dimethyl-1,3-propanediol in an adequate solvent such as for example an aromatic hydrocarbon $(C_6-C_8)$ and at high temperatures.

The preparation of zinc derivatives of formula (VIa) such as the 3-(1-adamantyl)-4-methoxybenzene zinc chloride can be carried out, for example, by lithiation of the 3-(1-adamantyl)-1-bromo-4-methoxybenzene at low temperature, followed by treatment with $ZnCl_2$.

Preferably, the transition metal compound to carry out the coupling between a compound of formula (III) and a compound of formula (IV) to yield the compound of formula (II) is selected from the metal salts and metal complexes of palladium and nickel. Examples of adequate metal compounds are: tetrakis(triphenylphosphine)palladium (0), $(Pd(PPh_3)_4)$; dichloro[1,1'-bis(diphenylphosphine)ferrocene]palladium (II), $(PdCl_2(dppf))$; dichloro[1,4-bis(diphenylphosphine)butane]palladium, $(PdCl_2(dppb))$; dichlorobis(tricyclohexylphosphine) palladium (II) $(PdCl_2(PCy_3)_2)$; dichloro[1,1'-bis(di-terc-buthylphosphine)ferrocene]palladium (II), $(PdCl_2(dtbp))$; palladium; palladium chloride; palladium acetate; dichlorobis(triphenylphosphine)nickel (II), $NiCl_2(PPh_3)_2$; and mixtures of the above mentioned catalysts with phosphines; and palladium catalysts on polymeric supports. Preferably, the metal compound is the tetrakis(triphenylphosphine)palladium (0), $(Pd(PPh_3)_4)$.

Preferably, the base used for the Suzuki coupling is selected from an alkaline metal carbonate such as sodium or potassium carbonate and an alkaline metal phosphate such as sodium or potassium phosphate. More preferably, the base is the potassium phosphate. Preferably, it is carried out at a temperature comprised between room temperature and the reflux temperature of the solvent used.

The compounds of formula (II) are intermediates useful for the preparation of 1-adamantane derivatives, or of a pharmaceutically acceptable salt thereof. In particular, the compounds of formula (IIa) are especially useful for the preparation of Adapalene.

According to a third aspect of the present invention, it is provided a compound of formula (IIa) wherein X is a leaving group adequate to carry out a metallation/carboxylation, selected from Cl, Br and I. Preferably, the compound of formula (IIa) is that in which X is Br.

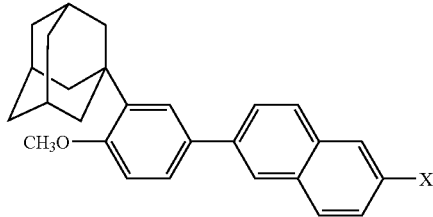

(IIa)

An advantage of the present invention lies in the fact that this preparation process of 1-adamantane derivatives provides a short, efficient and selective synthesis. In particular, the preparation of Adapalene by this process is particularly advantageous in its practical industrial application since these benzonaphthalenic intermediates are obtained from halogenonaphthalenic intermediates which are common and commercial, and therefore it is avoided the use of naphthalenecarboxylic derivatives which are expensive and difficult to obtain. Moreover, the final product is obtained with high chemical purity. An additional advantage of the process of the present invention lies in the fact that the protection/deprotection steps of the carboxylic group are avoided.

Additional objects, advantages and features of the invention will become apparent to those skilled in the art upon examination of the description or may be learned by practice of the invention. Throughout the description and claims the word "comprise" and variations of the word, are not intended to exclude other technical features, additives, components, or steps. The disclosure in the abstract of this application is incorporated herein as reference. The following examples and drawings are provided by way of illustration, and they are not intended to be limiting of the present invention.

EXAMPLES

Unless it is indicated otherwise, all reactants were used as received from the respective commercial companies. The tetrahydrofurane (THF) and dioxane were distilled on Na/benzophenone and toluene on Na. $K_3PO_4$ was finely grinded before using it. The dry $CO_2$ flow was obtained by sublimation of solid $CO_2$ through tubes containing $CaCl_2$.

Example 1

Preparation of 6-bromo-2-naphthalenyl trifluoromethanesulphonate

Triflic anhydride [$(CF_3SO_2)_2O$, 1.8 ml, 3.03 g, 10.8 mmol] was added to a solution of 6-bromo-2-naphthol (2 g, 9.0 mmol) and triethylamine ($NEt_3$) (1.52 ml, 1.09 g, 10.8 mmol) in dichloromethane ($CH_2Cl_2$) (40 ml) and under inert atmosphere at $-10°$ C. After 2 h of stirring at $-10°$ C., the reaction mixture was diluted in $H_2O$ (50 ml) and extractions with $CH_2Cl_2$ (3×40 ml) were carried out. The joined organic phases were washed with aq HCl (50 ml, 0.1 M), followed with $H_2O$ (50 ml) and were dried on $Na_2SO_4$. The filtration, evaporation and purification by column chromatography ($SiO_2$, $CH_2Cl_2$) gave the title compound (3.25 g) as a colourless oil. IR (KBr) 3090, 1590, 1501, 1425, 1363, 1251, 1212, 1182, 1141, 1111, 1065, 960, 915, 882, 850, 801, 786, 767, 714, 653 y 609. M/Z (IQ, $NH_3$) 356 [M+($^{81}$Br), 53%], 354 [$M^+$ ($^{79}$Br), 63], 223 [M-$SO_2CF_3^+$ ($^{81}$Br), 63] y 221 [M-$SO_2CF_3^+$ ($^{79}$Br), 100].

Example 2

Preparation of 2,4,6-tris[3-(1-adamantyl)-4-methoxyphenyl]-1,3,5,2,4,6-trioxatriborinane n-BuLi (9 ml, 22.4 mmol, 2.5 M in hexane) was added to a solution of 3-(1-adamantyl)-1-bromo-4-methoxybenzene (6 g, 18.7 mmol) in THF (90 ml) at $-78°$ C. and under inert atmosphere during a period of 10 minutes. The reaction mixture was stirred at the same temperature during one hour, during this time a white precipitate was formed. The precipitate was dissolved with the addition of $B(O\text{-}i\text{-}Pr)_3$ (15 ml, 65.4 mmol) at $-78°$ C. After one hour of stirring at $-78°$ C., the reaction mixture was brought at room temperature and was agitated during 16 h. Next, the mixture was cooled at 0° C. and $H_2O$ (6 ml) and HCl (6 ml, 2M) were added. After 5 minutes, HCl (120 ml, 2M) was added again and it was kept at vigorous stirring during 10 minutes. Finally, extractions with AcOEt (3×100 ml) were carried out. The joined organic phases were dried with $Na_2SO_4$, filtered and after evaporation to dryness the crude 3-(1-adamantyl)-4-methoxyphenylboronic acid was obtained (6.46 g, which contains some trimer) as a yellow solid.

The obtained solid was suspended on hexane (60 ml) and the obtained suspension was heated at 50° C. during 30 minutes. Next, the suspension was allowed to cool at room temperature, was filtered and the solid was washed with hexane (30 ml). Once vacuum dried, the title compound was obtained (5.53 g) as a white solid which was used in the following Suzuki couplings without previous purification. IR (KBr) 3228, 2902, 2846, 1597, 1453, 1400, 1339, 1281, 1235, 1181, 1138, 1100, 1022, 820, 758 y 724. $^1$H RMN (400 MHz, $CDCl_3$) 8.15 (s, 1H), 8.05 (d, J=8.4 Hz, 1H), 7.00 (d, J=8.4 Hz, 1H), 3.92 (s, 3H), 2.21 (s, 6H), 2.10 (s, 3H) y 1.82 (s, 6H).

Example 3

Preparation of [3-(1-adamantyl)-4-methoxyphenyl]-5,5-dimethyl-1,3,2-dioxaborinane A solution of 2,4,6-tris[3-(1-adamantyl)-4-methoxyphenyl]-1,3,5,2,4,6-trioxatriborinane (1 g, 3.73 mmol) and 2,2-dimethyl-propane-1,3-diol (388 mg, 3.73 mmol) in toluene (10 ml) was heated at reflux, having the system Dean-Stark, and under inert atmosphere during 6 h. The toluene was evaporated at reduced pressure and cyclohexane (2 ml) was added. After heating the solution at reflux for 10 minutes, this was cooled at room temperature and the title product was obtained after filtration (904 mg, 68%) as a white solid, which was used in the following Suzuki couplings without previous purification. IR (KBr) 3217, 2958, 2900, 1596, 1477, 1416, 1377, 1310, 1283, 1233, 1177, 1136, 1100, 1032, 990, 816, 694, 676 y 633. M/Z (Electrospray) 355 ($M^+$).

Example 4

Preparation of 6-[3-(1-adamantyl)-4-methoxyphenyl]-2-bromonaphthalene 3-(1-adamantyl)-4-methoxyphenylboronic acid (150 mg, 0.32 mmol), 6-bromo-2-naphtalenyl trifluoromethanesulphonate (93 mg, 0.26 mmol), $K_3PO_4$ (222 mg, 1.05 mmol), KBr (34 mg, 0.29 mmol) and THF (2 ml) were introduced into a Schlenk tube. Next, the reaction mixture was deoxygenated (3 froze/thaw cycles). Next, $Pd(PPh_3)_4$ (15 mg, 0.013 mmol) was added and the mixture was again deoxygenated (2 froze/thaw cycles). After heating at reflux for 18 h, the mixture was brought at room temperature and was diluted with $CHCl_3$ (5 ml). The solution was filtered through celite and washings with $CHCl_3$ (2×5 ml) were carried out. The evaporation of the joined organic phases gave a residue which was redissolved in $CHCl_3$ (5 ml) and washed with $H_2O$ (2×5 ml). The organic phase was dried with $Na_2SO_4$ and after evaporation to dryness, a crude was obtained (97 mg) which was recrystallized with the minimum volume of toluene at reflux. The title compound was obtained (68 mg, 58%) as a pale yellow powder. IR (KBr) 2900, 2847, 1600, 1489, 1456, 1442, 1262, 1237, 1178, 1142, 1103, 1061, 1026, 877, 809 y 470. M/Z (EI) 448 [$M^+$ ($^{81}Br$), 76%] y 446 [$M^+$ ($^{79}Br$), 100].

Example 5

Preparation of 6-[3-(1-adamantyl)-4-methoxyphenyl]-2-bromonaphthalene 2,4,6-tris[3-(1-adamantyl)-4-methoxyphenyl]-1,3,5,2,4,6-trioxatriborinane (151 mg, 0.56 mmol), 6-bromo-2-naphthalenyl trifluoromethanesulphonate (100 mg, 0.28 mmol), $K_3PO_4$ (239 mg, 1.13 mmol), THF (2 ml) and $H_2O$ (0.4 ml) were introduced into a Schlenk tube. Next, the mixture was deoxygenated (3 froze/thaw cycles). Next, $Pd(PPh_3)_4$ (16 mg, 0.014 mmol) was added and the reaction mixture was again deoxygenated (2 froze/thaw cycles). After heating at reflux for 15 h, the mixture was diluted in toluene (5 ml) while it was still hot. The solution was filtered through celite and it was washed with hot toluene (2×5 ml). The joined organic phases were washed with hot $H_2O$ (2×5 ml). The organic phase was evaporated to dryness and gave a crude (201 mg) which was recrystallized with the minimum volume of toluene at reflux (1.2 ml), giving the title compound (107 mg, 85%) as a pale yellow powder. The spectroscopic data coincide with those of the Example 4.

Example 6

Preparation of 6-[3-(1-adamantyl)-4-methoxyphenyl]-2-bromonaphthalene

[3-(1-adamantyl)-4-methoxyphenyl]-5,5-dimethyl-1,3,2-dioxaborinane (100 mg, 0.28 mmol), 6-bromo-2-naphthalenyl trifluoromethanesulphonate (67 mg, 0.19 mmol), $K_3PO_4$ (160 mg, 0.75 mmol), THF (2 ml) and $H_2O$ (0.4 ml) were introduced in a Schlenk tube. The reaction mixture was deoxygenated (3 froze/thaw cycles). Next, $Pd(PPh_3)_4$ (11 mg, 0.009 mmol) was added and the mixture was again deoxygenated (2 froze/thaw cycles). After heating at reflux for 17 h, the mixture was diluted in toluene (5 ml) while it was still hot. The solution was filtered through celite and it was washed with hot toluene (2×5 ml). The joined organic phases were washed with hot $H_2O$ (2×5 ml). The organic phase was evaporated and a crude (59 mg) was obtained, which was recrystallized with the minimum volume of toluene at reflux (0.55 ml), giving the title compound (20 mg, 24%) as a pale yellow powder. The spectroscopic data coincide with those of the Example 4.

Example 7

Preparation of 6-[3-(1-adamantyl)-4-methoxyphenyl]-2-bromonaphthalene 2,4,6-tris[3-(1-adamantyl)-4-methoxyphenyl]-1,3,5,2,4,6-trioxatriborinane (187 mg, 0.70 mmol), 2,6-dibromonaphthalene (100 mg, 0.35 mmol), $K_3PO_4$ (296 mg, 1.4 mmol), THF (2 ml) and $H_2O$ (0.4 ml) were introduced in a Schlenk tube. The reaction mixture was deoxygenated (3 froze/thaw cycles). Next, $Pd(PPh_3)_4$ (20 mg, 0.017 mmol) was added and the mixture was again deoxygenated (2 froze/thaw cycles). After heating at reflux for 15 h, the reaction mixture was diluted in toluene (5 ml) while it was still hot. The mixture was filtered through celite and it was washed with hot toluene (2×5 ml). The joined organic phases were washed with hot $H_2O$ (2×5 ml). The organic phase was evaporated and a crude (128 mg) was obtained, which was recrystallized with the minimum volume of toluene at reflux (0.75 mL), giving the title compound (39 mg, 25%) as a pale yellow powder. The spectroscopic data coincide with those of the Example 4.

Example 8

Preparation of 6-[3-(1-adamantyl)-4-methoxyphenyl]-2-bromonaphthalene t-BuLi (159 µl, 1.4 M, 0.22 mmol) was added, dropwise, onto a mixture of 3-(1-adamantyl)-1-bromo-4-methoxybenzene (50 mg, 0.16 mmol) and anh. THF (1 ml) under atmosphere of Ar and at −78° C., and the mixture was kept in stirring for 1 hour. After this time, the reaction was allowed to evolve at room temperature, a solution of $ZnCl_2$ (21 mg, 0.16 mmol) in anhydrous THF (0.4 mL) was added and was stirred for 1 more hour. Next, a solution of 6-bromonaphthalenyl trifluoromethanesulphonate (40 mg, 0.13 mmol), $Pd(PPh_3)_4$ (9 mg, 0.008 mmol) and anh. THF (0.2 ml) was added and the reaction was kept at room temperature for 16 h. Finally, the reaction was neutralized with HCl (1 M) and extractions with $Et_2O$ (3×2 ml) were carried out. The organic phase was washed with sat NaCl (3×3 ml) and $H_2O$ (3×3 ml), was dried with $MgSO_4$ and was evaporated to dryness. A crude (58 mg) in form of a yellow solid was obtained, which was recrystallized with the minimum volume of toluene at reflux (0.2 ml), giving the title compound (20 mg, 29%) as a pale yellow powder. The spectroscopic data coincide with those of the Example 4.

Example 9

Preparation of Adapalene

A mixture of 6-[3-(1-adamantyl)-4-methoxyphenyl]-2-bromonaphthalene (50 mg, 0.11 mmol) in THF (1 ml) was introduced into a Schlenk tube and was heated until its complete dissolution. Next, NaH (4.5 mg, 60% dispersion in mineral oil, 0.11 mmol) was added under argon atmosphere and at room temperature, and the mixture was stirred for 10 minutes. The obtained mixture was cooled to −60° C. and t-BuLi (1.7 M in penthane, 0.22 mmol) was added, dropwise, during a period of 30 minutes. Next, and at the same temperature, a continuous mild flow of $CO_2$ (anhydrous gas) was introduced in the reaction for 1 h. After bringing the reaction to room temperature during 30 minutes with continuous flow of $CO_2$, the mixture was diluted with aq HCl (5 ml, 2 M) and was vigorously stirred for 10 minutes. The resulting mixture was extracted with $CHCl_3$ (3×5 ml) and the joined organic phases were evaporated to dryness once dried with $Na_2SO_4$, giving the crude of Adapalene.

The obtained crude was dissolved in dichloromethane (DCM) (3 mL) and $H_2O$ (3 mL) and NaOH (75 μL, 1 eq., 1.5 M) was added. The mixture was brought at 55° C. and kept at reflux for 20 minutes. Next, extractions with $H_2O$ (2×3 mL) were carried out. The aqueous phase was washed with DCM (2×3 mL). DCM (3 mL) was added again and the mixture was stirred at reflux for 10 minutes once acidified with HCl (1 M) until pH=3-4. Finally, the phases were separated and the aqueous one was extracted with DCM (2×3 mL). The joined organic phases were dried with $Na_2SO_4$ and were evaporated to dryness giving Adapalene (19 mg, 41%).

Example 10

Preparation of Adapalene

A mixture of 6-[3-(1-adamantyl)-4-methoxyphenyl]-2-bromonaphthalene (50 mg, 0.11 mmol), THF (1 ml) was introduced into a Schlenk tube and was heated until its complete dissolution. Next, NaH (4.5 mg, 60% dispersion in mineral oil, 0.11 mmol) was added under argon atmosphere and at room temperature, and the mixture was stirred for 10 minutes. The solution was cooled to −40° C. and n-BuLi (139.5 μl, 1.6 M in hexane, 0.22 mmol) was added, dropwise, during 30 minutes. At the same temperature, a continuous mild flow of $CO_2$ (anhydrous gas) was introduced in the reaction for 1 h. After bringing the reaction to room temperature during 30 minutes with continuous flow of $CO_2$, the mixture was diluted with aq HCl (5 ml, 2 M) and was vigorously stirred for 10 minutes. The resulting mixture was extracted with $CHCl_3$ (3×5 ml) and the joined organic phases were dried with $Na_2SO_4$ and next were evaporated to dryness, giving the crude of Adapalene. The crude was purified in the same way as that of the Example 8. 15 mg of Adapalene were obtained (30%) as a white solid.

The invention claimed is:

1. A compound of formula (IIa)

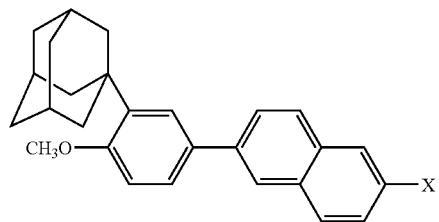

(IIa)

wherein X is a leaving group adequate to carry out a metallation/carboxylation where X is selected from Cl, Br and I.

2. The compound, according to claim 1, where X is Br.

* * * * *